United States Patent [19]

Haag et al.

[11] Patent Number: 5,015,778

[45] Date of Patent: May 14, 1991

[54] CATALYTIC METHOD TO PRODUCE HYDROXY SUBSTITUTED ARYLOPHENONES

[75] Inventors: Anthony P. Haag; E. W. Otterbacher, both of Midland, Mich.

[73] Assignee: The Dow Chemical Company, Midland, Mich.

[21] Appl. No.: 452,452

[22] Filed: Dec. 18, 1989

[51] Int. Cl.$^5$ .................................. C07C 45/36
[52] U.S. Cl. ........................ 568/319; 568/321
[58] Field of Search ............... 568/320, 321, 319

[56] References Cited

U.S. PATENT DOCUMENTS

| | | | |
|---|---|---|---|
| 1,389,288 | 8/1975 | d'Ostrowick et al. | 260/592 |
| 1,789,926 | 1/1931 | Binapfl et al. | 568/321 |
| 2,859,247 | 11/1958 | Radzitzky et al. | 260/590 |
| 3,038,940 | 6/1962 | Serres et al. | 260/590 |
| 3,073,866 | 1/1963 | Stanley | 260/591 |
| 3,162,683 | 12/1964 | Jones et al. | 260/254 |
| 3,280,181 | 10/1966 | Notarbartolo et al. | |
| 3,403,183 | 12/1966 | Dobratz et al. | 260/591 |
| 3,502,718 | 3/1970 | Welch | 260/254 |
| 3,562,318 | 2/1971 | Barone et al. | 260/524 |
| 3,584,038 | 6/1971 | Barone et al. | 260/524 R |
| 3,642,906 | 2/1972 | Kahn | 568/321 |
| 3,665,030 | 5/1972 | d'Ostrowick et al. | 260/488 CD |
| 3,875,237 | 4/1975 | Niynik | 568/321 |
| 4,175,098 | 11/1978 | Miyukami et al. | 568/321 |
| 4,218,400 | 8/1980 | Finger | 568/321 |
| 4,297,514 | 10/1981 | Ma | 568/321 |
| 4,299,987 | 10/1981 | Dolhyj et al. | 568/321 |
| 4,453,016 | 6/1984 | Au et al. | 568/432 |
| 4,624,758 | 11/1986 | Lysenko et al. | 204/78 |

FOREIGN PATENT DOCUMENTS

| | | | |
|---|---|---|---|
| 12939 | 12/1979 | European Pat. Off. | |
| 69598 | 7/1982 | European Pat. Off. | |
| 57503 | 8/1982 | European Pat. Off. | |
| 54032459 | 8/1977 | Japan . | |
| 59-219248 | 5/1983 | Japan . | |
| 58-126829 | 7/1983 | Japan . | |
| 59-001438 | 1/1984 | Japan . | |
| 59-219249 | 12/1984 | Japan . | |
| 62-240642 | 10/1987 | Japan | 568/320 |
| 529149 | 12/1976 | U.S.S.R. . | |

OTHER PUBLICATIONS

Sheldon et al., Metal Catalyzed Oxidations of Organic Compounds, pp. 368–382, Academic Press 1981.
Patai, The Chemistry of the Hydroxy Group, Part I, pp. 560–567; Interscience Publishers 1971.
Chemical Abstract 50:15489i.
Chemical Abstract 56:6638g.

*Primary Examiner*—James H. Reamer

[57] ABSTRACT

Hydroxy substituted arylophenones in general, and 4,4'-dihydroxybenzophenones in particular, are produced by catalytic oxidation of diaryl compounds containing hydroxy substituted diaryl moieties in a liquid medium. Oxidation occurs by contact of the diaryl compounds with an oxygen-containing gas in the presence of a solvent, base, a metal atom catalyst, and optionally, activated carbon. The arylophenones produced are useful as monomers in the production of epoxy and polycarbonate resins.

32 Claims, No Drawings

CATALYTIC METHOD TO PRODUCE HYDROXY SUBSTITUTED ARYLOPHENONES

FIELD OF THE INVENTION

This invention concerns a catalytic method for producing hydroxy substituted arylophenones, and in particular, a method for producing 4,4'-dihydroxybenzophenones.

BACKGROUND OF THE INVENTION

Hydroxy substituted arylophenone derivatives are commercially useful in synthetic plastics. For example, 4,4'-dihydroxybenzophenones are useful as monomers in the production of epoxy and polycarbonate resins. See, e.g., Lysenko et al., *Electrocatalytic Method for Producing Dihydroxybenzophenones*, U.S. Pat. No. 4,624,758 (Nov. 25, 1986). Epoxy resins useful in coatings, adhesives and casting resins are made by reacting a bisphenol, such as a 4,4'-dihydroxybenzophenone, with an epihalohydrin. Polycarbonate resins useful in coatings and casting resins are made by reacting a bisphenol and phosgene.

The method of producing dihydroxybenzophenones taught by Lysenko et al. includes the electrocatalytic oxidation of bis(4-hydroxyphenyl)methanes using a 2,3-diohloro-5,6-dicyano-1,4-benzoquinone oxidation catalyst. Although the process works well, the oxidation catalyst is not commercially available in large quantities and the process requires electricity, an expensive raw material.

European Patent No. 69,598 issued to Dahl et al. teaches production of hydroxy substituted arylophenones by reacting phenol with hydroxy substituted aryl acid halides or hydroxy substituted aryl carboxylic acids and esters thereof. The reaction takes place in the presence of a Lewis acid catalyst, such as boron trifluoride, and a strong acid.

Other methods are known for producing hydroxy substituted arylophenones. For example, Rose et al., *Production of Dihydroxy Arylophenones*, U.S. Pat. No. 4,433,172 (Feb. 21, 1984), teach the production of hydroxy substituted arylophenones by reacting diaryl carbonates with fluoroalkanesulfonic acids. Japanese Patent JP 5,901,438 (January 6, 1984), teaches the production of 4,4'-dihydroxybenzophenone by a two step process. In step one, a bis(4-trichloromethylphenyl)carbonate is reacted with phenol in the presence of a Lewis acid catalyst to produce a 4,4'-(4-hydroxybenzoyl)phenyl carbonate intermediate. This intermediate is subjected to alkali hydrolysis in a second step to produce the desired benzophenone. Stanley teaches, in *Process of Preparing Hydroxy-Alkoxy Arylophenones*, U.S. Pat. No. 3,073,866 (Jan. 15, 1963), production of hydroxy and alkoxy substituted arylophenones by condensing a hydroxy aryl carboxylic acid with an alkyl ether of phenol in the presence of phosphorous trichloride, zinc chloride, and a phosphoric acid solvent.

As can be seen, a need exists for a method capable of producing commercial quantities of hydroxy substituted arylophenones economically and at a reasonably high yield.

SUMMARY OF THE INVENTION

The present method for producing hydroxy substituted arylophenones comprises contacting a diaryl compound having at least one diaryl moiety with an oxygen-containing gas in a liquid medium. Each diaryl moiety comprises two aryl groups linked by an oxidizable carbon atom. At least one aryl group of the diaryl compound has at least one hydroxy group substituent. The liquid medium comprises a combination of liquid and solid components, the components being at least one base, at least one solvent, a catalytic amount of a metal atom catalyst and, optionally, activated carbon. The contact is conducted under conditions sufficient to produce a hydroxy substituted arylophenone.

DETAILED DESCRIPTION OF THE INVENTION

Diaryl compounds containing at least one diaryl moiety beneficially correspond to Formula 1:

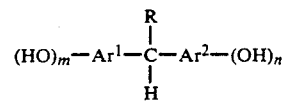

wherein:

R is selected from the group consisting of hydrogen, hydroxy, cyano, methyl, acylamide, carboxyl, lower alkoxy groups, lower alpha-hydroxy substituted alkyl groups, lower alkyl carboxylate groups, and a moiety represented by Formula 2:

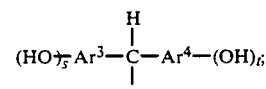

C is, in each instance, an oxidizable carbon atom;

$Ar^1$, $Ar^2$, $Ar^3$ and $Ar^4$ are aryl groups as defined hereinafter: and n, m, s, and t are each selected from the group consisting of zero and positive integers, such that the sum of n, m, s, and t is at least one. The diaryl compounds are discussed in greater detail hereinafter.

Each aryl group (Ar) represented herein is an aromatic moiety selected from the arene group, a major class of unsaturated cyclic hydrocarbons containing one or more aromatic rings. An arylgroup may be heterocyclic, but is preferably hydrocarbyl. Where a plurality of aromatic rings are present, they may be fused, as for example in the case of naphthalene, indene and anthracene; or covalently bonded to each other by way of a single bond, as for example in the case of biphenyl: or two aromatic rings may be connected through covalent bonding with a linking group, as for example in the case where a carbonyl group links together two benzene rings. Suitable linking groups include, for example, a carbonyl group, a sulfonyl group, an oxygen atom or a sulfur atom. Unless specified otherwise herein, the term "aromatic ring" should be construed broadly as referring to either a single aromatic ring or a plurality of aromatic rings which are fused together. Aryl groups can be the same or different. Each aryl group beneficially contains no more than about 18 carbon atoms, desirably no more than about 12 carbon atoms and preferably no more than about 6 carbon atoms. The most preferred aryl group is a benzene ring.

The number of hydroxy group substituents on an aryl group is not particularly critical, so long as at least one aryl group of the diaryl compound has at least one hydroxy group substituent. The hydroxy substituents, upon oxidation of the diaryl compound, yield a hydroxy substituted arylophenone product useful in producing epoxy or polycarbonate resins. The number of hydroxy group substituents on an aryl group is represented in Formulas 1 and 2 by the subscripts m, n, s, and t. The number of hydroxy groups is beneficially no greater than about three per aryl group. An individual aryl group may or may not have a hydroxy group substituent, or it may have a plurality of attached hydroxy groups. In a preferred embodiment, each aryl group has one hydroxy group substituent.

It is believed that position of the hydroxy group substituents on the aryl groups is not critical to achieve satisfactory results. In preferred embodiments where an aryl group is a benzene ring, the hydroxy groups are located in a position para or ortho with respect to the oxidizable carbon atoms.

The aryl groups may have other substituents thereon which do not significantly interfere with oxidation of the oxidizable carbon atom. These other substituents can be the same or different and may vary from one aryl group to another. Suitable substituents are hydrogen, halogens, alkoxy and alkyl groups wherein the alkoxy and alkyl groups have no more than about six carbon atoms. Examples of suitable alkoxy groups are methoxy, ethoxy, propoxy, isopropoxy, n-butoxy, secbutoxy, isobutoxy, tert-butoxy, cyclohexoxy and the like. Examples of suitable alkyl groups are methyl, ethyl, propyl, isopropyl, n-butyl, sec-butyl, tert-butyl and so on. Preferred substituents are hydrogen and halogens, with hydrogen being the most preferred substituent. Preferred halogens are fluorine, chlorine and bromine. Where a substituent is an alkyl or alkoxy group, it desirably has no more than about four carbon atoms and preferably no more than one carbon atom.

As used herein with respect to substituents suitable as an R group, the term "lower" refers to a carbon atom content of from one to about ten. The carboxyl, lower alkyl carboxylates, cyano and acylamide groups are attached to the oxidizable carbon atom by a covalent bond. By the term "cyano group", it is meant a —CN group. By the term "carboxyl group", it is meant a —COOH group. By the term "alkyl carboxylate group", it is meant a —COOZ group, wherein the Z refers to an alkyl group having up to about nine carbon atoms. By the term "acylamide group", it is meant a —CONH$_2$ group. Lower alkyl carboxylates suitable as an R group include methoxy carbonyl, ethoxy carbonyl, n-propoxy carbonyl and so on. Examples of lower alkoxy groups appear in the immediately preceding paragraph.

A suitable R group may also be a lower alkyl group having at least one hydroxy group bonded in a position alpha to the oxidizable carbon atom. Such alpha-hydroxy substituted lower alkyl groups may have additional hydroxy groups bonded thereto which are not in a position alpha to the oxidizable carbon atom. Examples of suitable lower alpha-hydroxy substituted alkyl groups include —CH$_2$OH, —CH(OH)—CH$_2$OH, —CH(OH)—(CH$_2$)$_v$—CH$_3$ and so on, wherein v is an integer selected such that the carbon atom content of the R group is about ten or less. Suitable alpha-hydroxy substituted alkyl groups also include cycloalkyl groups, such as a 1-hydroxy-cyclohexyl group.

Examples of suitable diaryl compounds containing diaryl moieties are bis(4-hydroxyphenyl)-methane, 2,2-bis(4-hydroxyphenyl)acetic acid, 2,2-bis(4-hydroxyphenyl)ethane, 2,2-bis(4-hydroxyphenyl)acetamide, 1,1,2,2-tetrakis(4-hydroxyphenyl)ethane and 1-hydroxy-2,2-bis(4-hydroxyphenyl)ethane.

Contact between the diaryl compound and the oxygen-containing gas is conducted in a liquid medium. The liquid medium comprises a combination of liquid and solid components, the components being at least one base, at least one solvent, a catalytic amount of a metal atom catalyst and, optionally, activated carbon. The liquid medium may also contain dissolved gases, such as oxygen. In preferred embodiments, the solvent is a liquid component which constitutes a significant portion of the liquid medium, while the base, metal atom catalyst and activated carbon are solid components which are either dissolved or dispersed therein. Use of agitation, such as by mechanical stirring, is advantageous in obtaining a more uniform dispersion of the solid components within the liquid components. The oxygen-containing gas is introduced by any convenient method, such as sparging. The diaryl compound may be introduced into the liquid medium as a solid which is either dissolved or dispersed therein.

Use of a solvent in maintaining a liquid medium enhances contact between the diaryl compound and molecular oxygen, as diaryl compounds are generally solids under reaction conditions described hereinafter. Suitable solvents are those which are inert with respect to the oxidation reaction and remain substantially in a liquid phase under reaction conditions. The solvent should be capable of dissolving the diaryl compound employed in the oxidation reaction. The solvent is preferably capable of dissolving other reactants as well, such as the base and metal atom catalyst.

Examples of suitable solvents are alcohols, ethers, halogenated hydrocarbons, amines, dimethylformamide, dimethylsulfoxide and the like. Preferred solvents are alcohols such as methanol, ethanol, propanol, isopropanol, butanol, tert-butanol, ethylene glycol and so on. Solvents may be utilized singly or in combination.

The choice of base is not critical, so long as its basicity is greater than the diaryl compound being oxidized. The base is suitably selected from the group consisting of alkali metal or alkaline earth metal hydroxides, alkali metal or alkaline earth metal alkoxides, alkali metal or alkaline earth metal amides and alkali metal or alkaline earth metal carbonates. Also suitable as a base are basic quaternary ammonium salts, such as tetra-alkylammonium hydroxides. Examples of bases are sodium hydroxide, potassium hydroxide, lithium hydroxide, magnesium hydroxide, calcium hydroxide, aluminum hydroxide and so on; sodium alkoxides, potassium alkoxides, lithium alkoxides, magnesium alkoxides, calcium alkoxides, aluminum alkoxides wherein the alkoxide may be methoxide, ethoxide, isopropoxide, tert-butoxide and the like: sodium amides, potassium amides, lithium amides, magnesium amides, calcium amides and aluminum amides. An example of a suitable basic quaternary ammonium salt is tetra-n-butylammonium hydroxide. Sodium hydroxide and potassium hydroxide are preferred bases due to ready availability and low cost. Bases may be used singly or in combination.

The proportion of base introduced into the liquid medium depends upon the amount of hydroxy group functionality bonded to the diaryl compound. A suitable range for the proportion of base employed is from about 1 equivalent to about 20 equivalents of base for each equivalent of hydroxy group functionality of the diaryl compound to be oxidized. It is undesirable to operate below the 1:1 ratio limit, because the yield and conversion of the resulting substituted arylophenone product is reduced and, therefore, provides an uneconomical result for commercial purposes. Better results are obtained when the proportion of base is increased. The preferred proportion of base ranges from about 2 equivalents to about 6 equivalents of base for each equivalent of hydroxy group functionality. Employing a proportion of base beyond the 20:1 ratio limit is operable, but not necessary to achieve satisfactory results.

The term metal atom catalyst is meant to refer to metallic elements, in either their metallic or ionic states, which are capable of catalyzing conversion of the diaryl compounds to arylophenones. Suitable metal atom catalysts include polyvalent heavy metals such as cobalt, copper, manganese, chromium or nickel atoms. The valence state of the metal atom catalyst is not critical and may, for example, be zero-, mono-, di- or trivalent. However, the most preferred metal atom catalysts are divalent or trivalent cobalt ions. The metal atom catalyst may be introduced into the liquid medium by addition of a soluble salt of the metal atom catalyst. Such metal atom catalyst salts may have either organic anions, such as carboxylates and the like, or inorganic anions such as halides, oxides, hydroxides or other inorganic acid anions. Examples of such metal atom catalyst salts are fluorides, chlorides, bromides, iodides, acetates, octylates, resinates, oxalates, stearates, naphthenates, nitrates, borates, phosphates, sulfates, carbonates, cyanides, oxides and hydroxide salts of cobalt, copper, manganese, chromium or nickel. The metal atom catalyst may also be introduced into the liquid phase in a metallic state. If introduced in a metallic state, the catalyst preferably is in a form which maximizes the surface area exposed in the liquid medium, such as a highly subdivided powder.

The proportion of metal atom catalyst introduced into the liquid medium is not critical, so long as it is present in an amount sufficient to promote or catalyze the oxidation reaction. The proportion suitably ranges from about 0.0001 to 1 equivalent per equivalent of oxidizable carbon atom functionality of the diaryl compound to be oxidized. The proportion of metal atom catalyst preferably ranges from about 0.001 to 0.1 equivalents per equivalent of oxidizable carbon atom functionality. It is possible to operate at greater than the 1:1 ratio limit, but there are no advantages realized in doing so. Below the 0.0001:1 ratio limit, the rate of reaction is uneconomically slow.

Activated carbon is optionally introduced into the liquid medium to enhance catalytic effects of the metal atom catalyst by increasing the oxidation reaction rate. The use of activated carbon in catalytic reactions is described by Au et al., *Preparation of Aromatic Aldehydes*, U.S. Pat. No. 4,453,016 (Jun. 5, 1984) at column 2, lines 36–53, the teachings of which are incorporated herein by reference. The activated carbon employed can be added in any available form such as powdered, crushed or briquette. The amount of activated carbon is not critical and an effective amount which will enhance the catalytic effects of the metal atom catalyst may be determined by those skilled in the art without undue experimentation. In general, a weight ratio of activated carbon to the diaryl compound in the range of from about 0.01:1 to about 0.1:1 is sufficient to cause enhanced catalytic effects. The activated carbon may be introduced into the liquid phase in any manner, such as those described in the Au et al. patent, which promotes good contact with the reactants contained therein.

Suitable oxygen-containing gases include pure molecular oxygen or mixtures of gases containing molecular oxygen, such as air. Air is preferred due to ready availability and low cost. The amount or concentration of molecular oxygen is not particularly critical and an appropriate amount may be determined without undue experimentation by the skilled artisan with due consideration being given to safety and convenience. In general, it is economically desirable to introduce oxygen in an amount sufficient to oxidize at least 20% by weight of the diaryl compound. It is preferred to introduce oxygen in an amount sufficient to maximize conversion of the diaryl compound to the desired arylophenone.

The oxidation reaction conveniently takes place at atmospheric pressure, but it is believed that pressures in excess of one atmosphere will increase the amount of oxygen dissolved in the liquid medium and, thereby, produce an increased reaction rate. Accordingly, pressures from about 1 atmosphere to about 100 atmospheres are suitable.

The oxidation reaction takes place desirably at a temperature of from about 60° C. to about 130° C. Operation outside of this range is possible, but does not provide optimum results. For example, above 130° C. the yield of substituted arylophenones decreases with only a small incremental increase in temperature. At temperatures below 60° C., the reaction proceeds at a slow rate. The reaction temperature preferably ranges from about 70° C. to about 100° C.

The time allowed for contact between the oxygen-containing gas and the diaryl compound should be sufficient to achieve a desired degree of conversion. The time required will vary depending upon the diaryl compound being oxidized, but a suitable time may be determined by those skilled in the art without undue experimentation. Generally, a time of about 10 hours results in maximum conversion to the desired arylophenone product. Shorter times result in decreased conversions to arylophenone products.

As illustrated by the examples which follow, the present invention is a method for producing hydroxy substituted arylophenones, such as a 4,4'-dihydroxybenzophenone. The method comprises contacting a diaryl compound having at least one diaryl moiety with an oxygen-containing gas, such as pure molecular oxygen or air, within a liquid medium. Each diaryl moiety comprises two aryl groups linked by an oxidizable carbon atom, such as the diphenyl structure of bis(4-hydroxyphenyl)methane. There is at least one aryl group on the compound having at least one hydroxy substituent. The contact occurs in the presence of at least one base, such as sodium hydroxide or potassium hydroxide: at least one solvent, such as ethylene glycol: a catalytic amount of a metal atom catalyst, such as atoms of cobalt, copper, nickel, chromium and manganese; and optionally, activated carbon. The contact occurs under conditions sufficient to produce a hydroxy substituted arylophenone, the conditions including a temperature of between about 60° C. and about 130° C. and a contact time of about 10 hours.

The arylophenones produced by the present method are preferably benzophenones corresponding to Formulas 3 (a) and (b):

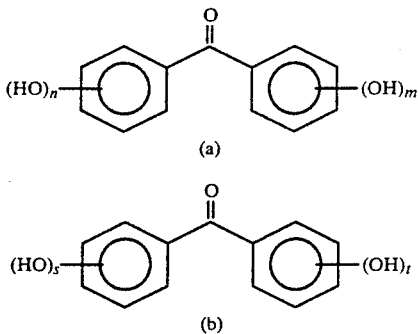

wherein n, m, s and t are each selected from the group consisting of zero and positive integers up to about three, such that their sum is at least one.

SPECIFIC EMBODIMENTS OF THE INVENTION

The following examples illustrate the present invention and should not be construed, by implication or otherwise, as limiting the scope thereof. All parts and percentages are by weight and all temperatures are in degrees Celsius (° C.) unless otherwise indicated hereinafter.

EXAMPLE 1

Oxidation of 1,1,2,2-tetrakis-(4-hydroxyphenyl)ethane to 4,4'-dihydroxybenzophenone The 1,1,2,2-tetrakis(4-hydroxyphenyl)ethane employed in this example is synthesized by a known method. It is prepared by loading 350 grams of phenol into a 500 milliliter Morton flask equipped with an overhead mechanical stirrer and heating mantle. The contents of the flask are heated to about 60° C., whereupon 2.3 grams of aqueous concentrated hydrochloric acid is added to the flask. After addition of the acid, 10.9 grams of an aqueous glyoxal solution containing glyoxal at about 40 grams per 100 milliliters of solution is added to the flask using a syringe pump operating at a flow rate of about 1.5 milliliters per hour. The contents of the flask are maintained at a temperature of about 60° C. for approximately 6.5 hours and then allowed to cool to room temperature overnight.

The reaction is continued the following day. Another 2.3 grams of concentrated hydrochloric acid and an additional 11.8 grams of the glyoxal solution are added to the flask. The glyoxal solution is, however, added in a single amount, as opposed to the previous use of a syringe pump. The flask is heated again to about 60° C. for about five hours. The excess phenol is then flash distilled from the reaction mixture, leaving a very viscous residue. The maximum still bottom temperature achieved during distillation is 120° C. at 30 millimeters of mercury. The residue is mixed with about 75 milliliters of tetrahydrofuran and heated to a temperature of from about 50° C. to about 66° C., i.e., the boiling point of tetrahydrofuran, thereby giving rise to a white precipitate. The solid is recovered by vacuum filtration followed by vacuum drying at 60° C. for about seven hours. The product is about 15 grams of an off-white solid which is confirmed as 1,1,2,2-tetrakis(4-hydroxyphenyl)ethane by high performance liquid chromatography, hereinafter termed "HPLC". The resulting product has a 1,1,2,2-tetrakis(4-hydroxyphenyl)ethane purity of about 79%. The yield is 23% based upon the amount of glyoxal charged to the flask.

The synthesized 1,1,2,2-tetrakis(4-hydroxyphenyl)ethane compound is then oxidized according to the present invention. In a nitrogen atmosphere, 1.2 grams of sodium hydroxide pellets and 19 milliliters of an ethylene glycol solvent are introduced into a 50 milliliter, three neck, round bottom flask. The flask is equipped with an overhead mechanical stirrer fitted with a Teflon ® (a trademark of the E. I. DuPont de Nemours Company) half-moon paddle, a reflux condenser, a heating mantle and a 25–50 micron fritted glass sparge tube. The mixture of ethylene glycol and sodium hydroxide pellets is stirred until the pellets dissolve to yield a uniform solution of solvent and base. After obtaining a uniform solution, 1.0 gram of the 1,1,2,2-tetrakis(4-hydroxyphenyl)ethane compound is added to the flask containing the base and solvent.

Following addition of the 1,1,2,2-tetrakis(4-hydroxyphenyl)ethane compound, 0.040 grams of $CoCl_2$ hexahydrate dissolved in 1 milliliter of ethylene glycol and 0.05 grams of pulverized activated carbon are added to the flask. Pure oxygen gas is introduced to the flask through the sparge tube at a rate of 41 milliliters per minute. The temperature of the flask containing the above-described mixture is regulated by the heating mantle and maintained at about 80° C. The reaction is conducted overnight for about 13 hours.

After conducting the reaction, the contents of the flask are diluted with 75 milliliters of water and filtered under vacuum. The filtrate is acidified to a pH of about 1.0 with concentrated hydrochloric acid. The product is isolated from the acidified filtrate into an organic phase by three separate and sequential extractions using about 10 milliliters of methyl isobutyl ketone for each extraction. The combined organic phase of about 30 milliliters is then washed with about 10 milliliters of water and concentrated in vacuo.

The isolated product is about 1.2 grams of an orange, oily appearing solid containing 52% by weight 4,4'-dihydroxybenzophenone, thereby giving a yield of 73% based on the amount of 1,1,2,2-tetrakis(4-hydroxyphenyl)ethane charged to the flask. The presence and amount of 4,4'-dihydroxybenzophenone is confirmed by HPLC analysis using a 4,4'-dihydroxybenzophenone standard compound purchased from the Aldrich Chemical Company.

EXAMPLE 2

Oxidation of 2,2-bis(4-hydroxyphenyl) acetic acid to 4,4'-dihydroxybenzophenone

The 2,2-bis(4-hydroxyphenyl) acetic acid compound used in this example is synthesized prior to oxidation. A one liter, three neck, Morton flask equipped with an overhead mechanical stirrer, heating mantle, sparge tube with coarse glass frit and an addition funnel is charged with 300 grams of phenol and heated with stirring to a temperature of about 52° C. The phenol is saturated with HCl gas by sparging the HCl gas into the phenol at a slow, gentle rate for about 15 minutes. The HCl sparge is followed by addition of 99.0 grams of a 50% aqueous glyoxylic acid solution through the addition funnel at a constant rate over a 30 minute period. The contents of the flask are not heated during the glyoxylic acid addition, due to exothermic heat evolution which maintains the flask's contents at a temperature of from about 45°–55° C. Thereafter, the contents are maintained at a temperature of about 50° C. for approximately five hours and then allowed to cool overnight with stirring.

The 2,2-bis(4-hydroxyphenyl)acetic acid product is isolated from the reaction mixture by flash distillation and subsequent purification of the still bottom residue. During distillation, the maximum pot temperature achieved is 134° C. at 18 millimeters of mercury. The pot residue is dissolved into a combined organic and inorganic mixture consisting of 300 milliliters of diethyl ether and an aqueous sodium bicarbonate solution prepared by dissolving 56 grams of sodium bicarbonate into 700 milliliters of water. The aqueous bicarbonate and ether phases are allowed to separate. The ether layer is isolated, washed with 50 milliliters of a 5% aqueous solution of sodium bicarbonate and the ether phase discarded. The combined aqueous bicarbonate phases are then washed with 20 milliliters of diethyl ether and acidified to a pH of about 1.0 by addition of concentrated aqueous hydrochloric acid. Product contained in the aqueous phase is then extracted with 100 milliliters of diethyl ether. The ether layer containing the product is washed with 30 milliliters of water and then concentrated in vacuo.

The isolated product is 143.8 grams of an orange crystalline solid having a purity of about 95%. The purity and identity of 2,2-bis(4-hydroxyphenyl) acetic acid is confirmed by HPLC analysis. The yield is 72% based upon the amount of glyoxylic acid charged to the flask.

The oxidation reaction procedure described in Example 1 is substantially repeated using 1.08 grams of the 2,2-bis(4-hydroxyphenyl)acetic acid compound synthesized as described in the preceding paragraphs. The flask is initially charged with 2.0 grams of sodium hydroxide pellets and 20 milliliters of ethylene glycol. After obtaining a homogeneous solution, the 1.08 grams of the 2,2-bis(4-hydroxyphenyl)acetic acid compound is added to the flask. Thereafter, a solution of 0.041 grams of $CoCl_2$ hexahydrate dissolved into 1 milliliter of ethylene glycol is added to the flask and followed by the addition of 0.05 grams of activated carbon. The reaction is conducted for about 19 hours. All remaining procedures are the same as in Example 1.

The product is 0.85 grams of a brown solid having a 4,4'-dihydroxybenzophenone content of about 69%, thereby giving a yield of 62% based on the amount of bis(4-hydroxyphenyl)acetic acid charged to the flask. The presence and amount of 4,4'-dihydroxybenzophenone is confirmed by HPLC analysis as in Example 1.

EXAMPLE 3

Oxidation of bis(4-hydroxyphenyl)methane to 4,4'-dihydroxybenzophenone

The oxidation procedure described in Example 1 is substantially repeated using bis(4-hydroxyphenyl) methane as the compound to be oxidized. The bis(4-hydroxyphenyl)methane is purchased from the Aldrich Chemical Company. The flask is initially charged with 3.8 grams of sodium hydroxide pellets and 28 milliliters of ethylene glycol. After obtaining a homogeneous solution, 2.51 grams of the bis(4-hydroxyphenyl)methane compound is added to the flask. Thereafter, a solution of 0.178 grams of $CoCl_2$ hexahydrate dissolved in 2 milliliters of ethylene glycol is added to the flask and followed by the addition of 0.22 grams of activated carbon. The reaction is conducted for about 24 hours. All remaining procedures are the same as in Example 1.

The product obtained is 2.9 grams of a brown solid containing 56% of 4,4'-dihydroxybenzophenone thereby giving a yield of 61% based on the amount of bis(4-hydroxyphenyl) methane charged to the flask. The presence and amount of 4,4'-dihydroxybenzophenone is confirmed by HPLC analysis as in Example 1.

EXAMPLE 4

Oxidation of 1-hydroxy-2,2-bis(4-hydroxyphenyl) ethane to 4,4'-dihydroxybenzophenone.

The 1-hydroxy-2,2-bis(4-hydroxyphenyl) ethane compound oxidized in this example is synthesized prior to oxidation. A 100 milliliter, three neck, round bottom flask equipped with a magnetic stirrer, heating mantle and sparge tube with coarse glass frit is charged with 37.6 grams of phenol and heated with stirring to a temperature of about 45° C. The phenol is saturated with HCl gas by sparging the HCl gas into the phenol at a slow, gentle rate for about 15 minutes. Simultaneous with the start of the HCl sparge is the addition of 4.8 grams of hydroxy-acetaldehyde dimer to the flask. The hydroxy-acetaldehyde dimer is obtained from the Aldrich Chemical Company. The contents of the flask are maintained at a temperature of about 45° C. during the addition and HCl gas sparge. Thereafter, the contents are maintained at a temperature of from about 45° C. to about 60° C. for approximately 2 hours.

The 1-hydroxy-2,2-bis(4-hydroxyphenyl)ethane product is isolated from the reaction mixture by flash distillation. During distillation, the maximum pot temperature achieved is 135° C. at 15 millimeters of mercury. The resulting still bottom residue weighs 19.1 grams and solidifies to a golden, transparent, glass-like solid. The presence of 1-hydroxy-2,2-bis(4-hydroxyphenyl)ethane as a major component of the still bottom residue is confirmed by HPLC analysis.

The oxidation procedure described in Example 1 is substantially repeated using 1.00 gram of the 1-hydroxy-2,2-bis(4-hydroxyphenyl)ethane compound synthesized in the preceding paragraphs. The flask is initially charged with 2.0 grams of sodium hydroxide pellets and 19 milliliters of ethylene glycol. After obtaining a homogeneous solution, the 1.00 gram of the 1-hydroxy-2,2-bis(4-hydroxyphenyl)ethane compound is added to the flask. Thereafter, a solution of 0.041 grams of $CoCl_2$ hexahydrate dissolved in 1 milliliter of ethylene glycol is added to the flask and followed by the addition of 0.05 grams of activated carbon. All remaining procedures are the same as in Example 1.

The presence of 4,4'-dihydroxybenzophenone as the major component of the reaction mixture is confirmed by HPLC analysis as in Example 1. The amount of 4,4'-dihydroxybenzophenone in the reaction mixture is not determined.

The foregoing examples illustrate that a variety of diaryl compounds may be oxidized to a arylophenone product according to the invention. Similar results are obtained in using the present invention with other reaction mixtures and process variations as previously disclosed herein.

The arylophenones produced according to the invention are useful as monomers in the production of epoxy and polycarbonate resins.

What is claimed is:

1. A method of producing hydroxy substituted arylophenones that comprises contacting a diaryl compound having at least one diaryl moiety with an oxygen-containing gas in a liquid medium, each diaryl moiety comprising two aryl groups linked by an oxidizable carbon atom, at least one aryl group of the diaryl compound having at least one hydroxy group substituent, the liquid medium comprising a combination of liquid and solid components, the components being at least one base having a basicity greater than the diaryl compound and which is present in an amount sufficient to yield at least about one equivalent of base for each equivalent of hydroxy group functionality of the diaryl compound, at least one inert solvent capable of dissolving the diaryl compound, a catalytic amount of a metal atom catalyst capable of catalyzing conversion of the diaryl compound to a hydroxy substituted arylophenone and, optionally, activated carbon, the contact being conducted under conditions sufficient to produce a hydroxy substituted arylophenone.

2. The method of claim 1 wherein the diaryl compound corresponds to the formula:

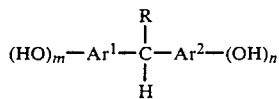

wherein:
R is selected from the group consisting of hydrogen, hydroxy, cyano, methyl, acylamide, carboxyl, lower alkoxy groups, lower alpha-hydroxy substituted alkyl groups, lower alkyl carboxylate groups, and a moiety represented by:

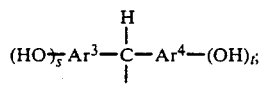

C represents, in each instance, an oxidizable carbon atom:
$Ar^1$, $Ar^2$, $Ar^3$ and $Ar^4$ are aryl groups; and
n, m, s, and t are each selected from the group consisting of zero and positive integers, such that the sum of n, m, s, and t is at least one.

3. The method of claim 1 wherein at least one aryl group is a benzene ring.

4. The method of claim 1 wherein at least one aryl group is a fused aromatic ring.

5. The method of claim 1 wherein at least one aryl group comprises a plurality of aromatic rings connected by covalent bonds.

6. The method of claim 1 wherein at least one aryl group comprises two aromatic rings bonded to each other by a linking group.

7. The method of claim 6 wherein the linking group is selected from the group consisting of carbonyl, sulfonyl, an oxygen atom and a sulfur atom.

8. The method of claim 1 wherein at least one aryl group has from one to about three hydroxy group substituents.

9. The method of claim 1 wherein at least one aryl group has at least one substituent selected from the group consisting of hydrogen, halogens, alkoxy groups, alkyl groups and combinations thereof.

10. The method of claim 1 wherein the oxidizable carbon atom has a substituent bonded thereto selected from the group consisting of hydrogen, hydroxy, cyano, methyl, acylamide, carboxyl, lower alkoxy groups, lower alpha-hydroxy substituted alkyl groups and lower alkyl carboxylate groups.

11. The method of claim 1 wherein the diaryl compound is selected from the group consisting of bis(4-hydroxyphenyl)methane, 2,2-bis(4-hydroxyphenyl)acetic acid, 2,2-bis(4-hydroxyphenyl)ethane, 2,2-bis(4-hydroxyphenyl)acetamide, 1,1,2,2-tetrakis(4-hydroxyphenyl)ethane, 1-hydroxy-2,2-bis(4-hydroxyphenyl)ethane and mixtures thereof.

12. The method of claim 1 wherein the diaryl compound corresponds to the formula:

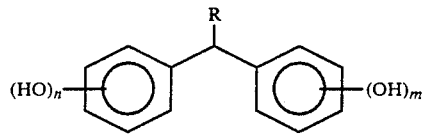

wherein:
R is selected from the group consisting of hydrogen, hydroxy, cyano, methyl, acylamide, carboxyl, lower alkoxy groups, lower alpha-hydroxy substituted alkyl groups, lower alkyl carboxylate groups and

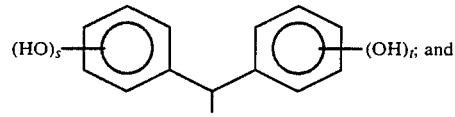

n, m, s, and t are each selected from the group consisting of zero and positive integers up to about three, such that the sum of n, m, s and t is equal to at least one.

13. The method of claim 1 wherein the metal atom catalyst is selected from the group consisting of atoms of cobalt, copper, manganese, chromium and nickel.

14. The method of claim 13 wherein the atoms are in a metallic form.

15. The method of claim 13 wherein the atoms are in an ionic form.

16. The method of claim 1 wherein the metal atom catalyst is a divalent or trivalent cobalt ion.

17. The method of claim 1 wherein from about 0.0001 equivalents to about 1 equivalent of metal atom catalyst is employed for each equivalent of oxidizable carbon atom functionality of the diaryl compound.

18. The method of claim 1 wherein the conditions include a temperature of from about 60° C. to about 130° C.

19. The method of claim 1 wherein the conditions include a temperature of from about 70° C. to about 100° C.

20. The method of claim 1 wherein the conditions include a pressure of from about 1 atmosphere to about 100 atmospheres.

21. The method of claim 1 wherein the solvent is selected from the group consisting of alcohols, ethers, halogenated hydrocarbons, dimethylformamide, dimethylsulfoxide, ethylene glycol and mixtures thereof.

22. The method of claim 1 wherein the base is selected from the group consisting of alkali metal or alkaline earth metal hydroxides, alkali metal or alkaline earth metal alkoxides, alkali metal or alkaline earth metal amides, alkali metal or alkaline earth metal carbonates, basic quaternary ammonium salts and mixtures thereof.

23. The method of claim 1 wherein the base is selected from the group consisting of sodium hydroxide, potassium hydroxide and mixtures thereof.

24. The method of claim 1 wherein the base is present in an amount from about 1 equivalent to about 20 equivalents for each equivalent of hydroxy group functionality of the diaryl compound.

25. The method of claim 1 wherein the base is present in an amount from about 2 equivalents to about 6 equivalents for each equivalent of hydroxy group functionality of the diaryl compound.

26. The method of claim 1 wherein the oxygen-containing gas is air.

27. The method of claim 1 wherein the arylophenone is a 4,4'-dihydroxybenzophenone.

28. The method of claim 1 wherein activated carbon is introduced into the liquid medium.

29. The method of claim 1 wherein the activated carbon introduced into the liquid medium corresponds to a weight ratio of activated carbon to the diaryl compound of about 0.01:1 to about 0.1:1.

30. The method of claim 1 wherein the conditions include a contact time of at least about 10 hours.

31. The method of claim 1 wherein the diaryl compound is selected from the group consisting of bis(4-hydroxyphenyl)methane, 2,2-bis(4-hydroxyphenyl) acetic acid, 2,2-bis(4-hydroxyphenyl)ethane, 2,2-bis(4-hydroxyphenyl)acetamide, 1,1,2,2-tetrakis(4-hydroxyphenyl)ethane, 1-hydroxy-2,2-bis(4-hydroxyphenyl) ethane and mixtures thereof; the oxygen-containing gas is selected from the group consisting of air and pure molecular oxygen; the base is selected from the group consisting of sodium hydroxide, potassium hydroxide and mixtures thereof; the solvent is selected from the group consisting of methanol, ethanol, propanol, isopropanol, butanol, tert-butanol, ethylene glycol, dimethylsulfoxide, dimethylformamide and mixtures thereof; the metal atom catalyst is selected from metal atom catalyst salts of cobalt, copper, manganese, chromium and nickel; and the conditions include a temperature of from about 70° C. to about 100° C.

32. A method for producing hydroxy substituted arylophenones that comprises contacting a diaryl compound with an oxygen-containing gas in a liquid medium, the diaryl compound corresponding to the formula:

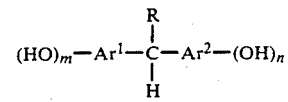

wherein:
R is selected from the group consisting of hydrogen, hydroxy, cyano, methyl, acylamide, carboxyl, lower alkoxy groups, lower alpha-hydroxy substituted alkyl groups, lower alkyl carboxylate groups, and a moiety represented by:

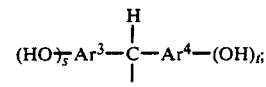

C represents, in each instance, an oxidizable carbon atom;
$Ar^1$, $Ar^2$, $Ar^3$ and $Ar^4$ are aryl groups; and
n, m, s, and t are each selected from the group consisting of zero and positive integers, such that the sum of n, m, s, and t is at least one, the liquid medium comprising a combination of liquid and solid components, the components being:
at least one base having a basicity greater than the diaryl compound and which is present in an amount sufficient to yield at least about one equivalent of base for each equivalent of hydroxy group functionality of the diaryl compound, the base being selected from the group consisting of alkali metal or alkaline earth metal hydroxides, alkali metal or alkaline earth metal alkoxides, alkali metal or alkaline earth metal amides, alkali metal or alkaline earth metal carbonates and basic quaternary ammonium salts;
at least one inert solvent capable of dissolving the diaryl compound and which is selected from the group consisting of alcohols, ethers, halogenated hydrocarbons, dimethylformamide, dimethylsulfoxide and ethylene glycol;
a catalytic amount of at least one metal atom catalyst capable of catalyzing conversion of the diaryl compound to a hydroxy substituted arylophenone and which is selected from the group consisting of atoms of cobalt, copper, manganese, chromium and nickel; and
optionally, an effective amount of activated carbon, the contact being conducted under a pressure of from about 1 atmosphere to about 100 atmospheres and a temperature of from about 60° C. to about 130° C.

* * * * *